(12) United States Patent
Romani et al.

(10) Patent No.: US 8,022,036 B2
(45) Date of Patent: Sep. 20, 2011

(54) USE OF THYMOSIN ALPHA 1 FOR THE TREATMENT OF IMMUNOLOGICAL DISEASES

(75) Inventors: Luigina Romani, Perugia (IT); Francesco Bistoni, Perugia (IT); Enrico Garaci, Rome (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 150 days.

(21) Appl. No.: 12/272,573

(22) Filed: Nov. 17, 2008

(65) Prior Publication Data

US 2009/0155260 A1 Jun. 18, 2009

Related U.S. Application Data

(63) Continuation-in-part of application No. PCT/EP2007/053321, filed on Apr. 4, 2007.

(30) Foreign Application Priority Data

May 19, 2006 (IT) ..................................... 06010441

(51) Int. Cl.
*A61K 38/32* (2006.01)
*A61K 39/00* (2006.01)

(52) U.S. Cl. ..................................... 514/12.9; 424/133.1

(58) Field of Classification Search .................. None
See application file for complete search history.

(56) References Cited

U.S. PATENT DOCUMENTS

| 5,308,833 | A | * | 5/1994 | Scharschmidt et al. | ......... 514/12 |
| 5,750,501 | A | * | 5/1998 | Chretien et al. | ................. 514/12 |
| 6,197,751 | B1 | | 3/2001 | Malinda et al. | |
| 2005/0058641 | A1 | * | 3/2005 | Siemionow | ................ 424/144.1 |

FOREIGN PATENT DOCUMENTS

| WO | 9512405 | 5/1995 |
| WO | 9835696 | 8/1998 |
| WO | 2005027958 | 3/2005 |

OTHER PUBLICATIONS

Turka et al. T-cell activation by the CD28 ligand B7 is required for cardiac allograft rejection in vivo. Proc Natl Acad Sci USA, 89:11102-11105 (1992).*
Blazer et al. FK506 inhibits graft-versus-host disease and bone marrow graft rejection in murine recipients of MHC disparate donor grafts by interfering with mature peripheral T cell expansion post-transplation. The Journal of Immunology 153:1836-1846 (1994).*
Ohta, et al., Thymosin alpha1 exerts protective effect against the 5-fu induced bone marrow toxicity, International Journal of Immunopharmacology, vol. 7(5), 1985, pp. 761-768.
Vasquez, et al., Avian thymic hormone treatment of peripheral blood mononuclear cells from young chicks stimulates acute graft-versus-host reaction in chicken embryos, Development and Comparative Immunology, vol. 29(7), 2005, pp. 663-668.
Romani, et al., Thymosin alpha1 activates dendritic cell tryptophan catabolism and establishes a regulatory environment for balance of inflammation and tolerance, Blood, vol. 108(7), 2006, pp. 2265-2274.

* cited by examiner

*Primary Examiner* — Marianne P Allen
*Assistant Examiner* — Regina M Deberry
(74) *Attorney, Agent, or Firm* — Lucas & Mercanti, LLP

(57) ABSTRACT

It is described the use of thymosin alpha 1 for preparing a medicament useful for the prevention or treatment of graft-versus-host disease or graft rejection reactions in organ transplantation, in a mammal subject, in which the cells, tissues or organs for transplant is selected from the group comprising: stem cells, hematopoietic stem cells, bone marrow, heart, liver, kidney, lung, pancreas, small intestine, cornea or skin.

14 Claims, 7 Drawing Sheets

Figure 1A:
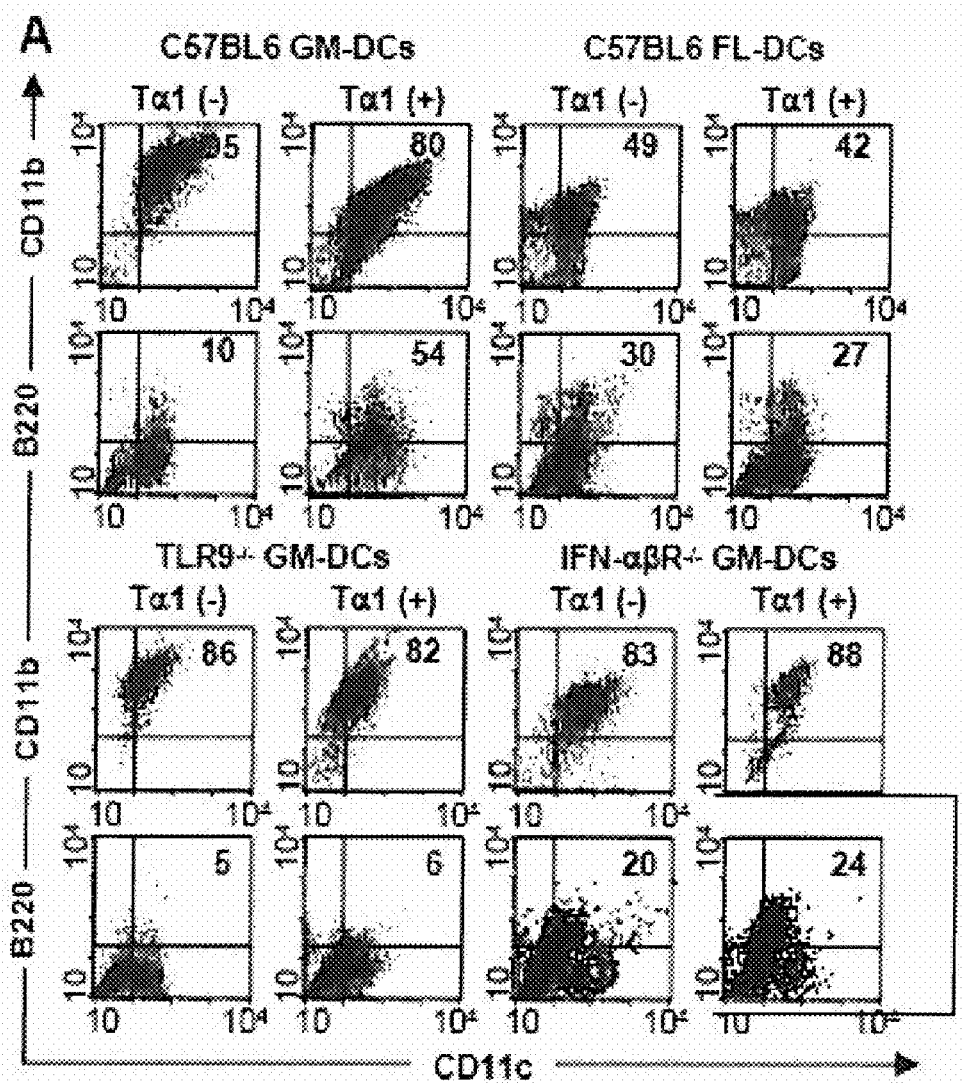

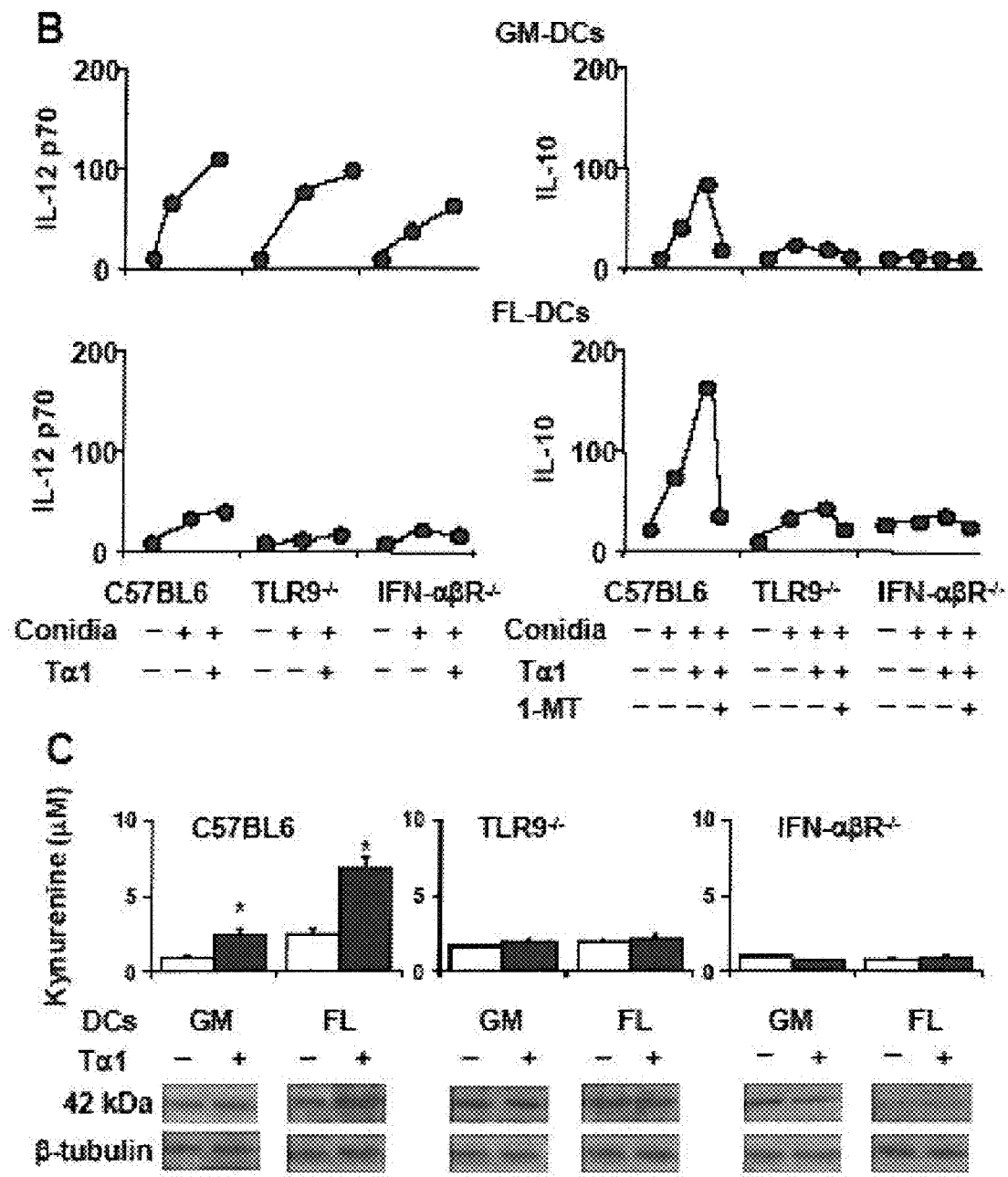
Fig 1B,C

USE OF THYMOSIN ALPHA 1 FOR THE TREATMENT OF IMMUNOLOGICAL DISEASES

CROSS-REFERENCE TO RELATED APPLICATIONS

This application is a continuation-in-part of PCT/EP2007/053321, filed Apr. 4, 2007, the contents of which are incorporated herein by reference. This application also claims the benefit of priority therefrom.

FIELD OF THE INVENTION

The present invention relates to the use of thymosin alpha 1 for preparing a medicament for the treatment of graft-versus-host disease.

BACKGROUND OF THE INVENTION

In bone marrow transplantation or blood transfusion, or organ transplantation from a donor to a recipient having no histocompatibility with the donor, the donor's lymphocytes migrate into the recipient. If the recipient cannot reject the donor's lymphocytes, the donor's lymphocytes take and proliferate in the recipient's body and attack tissues inducing a disease.

Patients with leukemia, end-stage renal, cardiac, pulmonary or hepatic failure, organ transplantation are quite commonly used in the treatment. For example, allografts (organ grafts harvested from donors other than the patient him/herself or host/recipient of the graft) of various types, e.g. kidney, heart, lung, liver, bone marrow, pancreas, cornea, small intestine and skin (e.g. epidermal sheets) are currently routinely performed. Xenografts (organ grafts harvested from non-human animals), such as porcine heart valves, are also being used clinically to replace their dysfunctional human counterparts.

To ensure successful organ transplantation, it is desirable to obtain the graft from the patient's identical twin or his/her immediate family member. This is because organ transplants evoke a variety of immune responses in the host, which results in rejection of the graft and graft-versus-host disease (hereinafter, referred to as "GVHD").

The immune response is primarily triggered by T cells through recognition of alloantigens, and the major targets in transplant rejection are non-self allelic forms of class I and class II Major Histocompatibility Complex (MHC) antigens. In acute rejection, donor's antigen-presenting cells such as dendritic cells and monocytes migrate from the allograft to the regional lymph nodes, where they are recognized as foreign by the recipient's CD4$^+$ T$_H$ cells, stimulating T$_H$ cell proliferation. Following T$_H$ cells proliferation, a population of effector cells (including cytotoxic CD8$^+$ T cells and CD4$^+$ T cells) is generated, which migrates and infiltrates to the graft and mediates graft rejection (Noelle et al. (1991) FASEB 5(13):2770).

Whereas acute rejection is a T cell-dependent process, a broad array of effector mechanisms participates in graft destruction. Through the release of cytokines and cell-to-cell interactions, a diverse assembly of lymphocytes including CD4$^+$ T cells, CD8$^+$ cytotoxic T cells, antibody-forming B cells and other proinflammatory leukocytes, is recruited into the anti-allograft response. Antigen-presenting graft cells are destroyed directly by cytotoxic CD8$^+$ T cells. Activated CD4$^+$ T cells produce interleukin-2 (hereinafter, referred to as "IL-2"), which is essential to the activation of both CD8$^+$ T cells and B cells. Additionally, CD4$^+$ T cells produce other cytokines such as IFN-γ and IL-4 that also contribute to the destruction of allograft. Furthermore, interferon-γ (hereinafter, referred to as "IFN-γ") induces increased expression of class I and class II MHC molecules on graft tissue, which is more readily attacked by alloreactive effector cells. IFN-γ enhances macrophage activity and affects many inflammatory cells leading to delayed-type-hypersensitivity reaction and inflammation causing nonspecific damage to the graft. These reactions appear to be the primary cause of the early acute rejection that may occur within the first few weeks after transplant. If untreated, acute rejection progresses to a rapid and severe process that causes destruction of the transplant within a few days.

On the other hand, when a T-lymphocyte from the donor recognizes the differences based on a set of genetic markers, generally referred to as human leukocyte antigens (HLA), and it starts to attack the new body, i.e., the patient's body. Although most patients and donors are matched as closely as possible for HLA markers. Many minor markers, however, differ between donors and patients except when the patient and donor are identical twins. Before a transplant, extensive typing of the donor and recipient is performed to make sure that the donor and recipient are very close immunologically. Despite this typing there are immunological differences that cannot be detected and that the T-lymphocytes in the donor graft are capable of detecting. As a result, the donor T-lymphocytes start to attack the patient's body and cause GVHD.

There are two forms of GVHD: the acute and chronic GVHD. Acute GVHD usually occurs within the first three months following a transplant. T-cells present in the donor's bone marrow at the time of transplant attack the patient's skin, liver, stomach, and/or intestines. The earliest signs of acute GVHD are usually a skin rash that appears on the hand, feet and face. Other than blistering skin, patients with severe GVHD also develop large amounts of watery or bloody diarrhea with cramping due to the donor's T-cells' attack on the stomach and intestines. Jaundice (yellowing of the skin and eyes) is the usual indication that GVHD disease involves the liver. The more organs involved and the worse the symptoms, the worse the GVHD disease.

In the case of bone marrow transplantation, in particular, GVHD is another obstacle to survival of transplanted patients. Storb (1984) "Pathophysiology and prevention of graft-versus-host disease." In Advances in Immunobiology: Blood cell antigens and bone marrow transplantation, McCullogh and Sandier, editors, Alan, Inc., N.Y., p.337.

A large proportion of GVHD-afflicted individuals die as a result of GVHD. Weiden et al. (1980) "Graft-versus-host disease in allogeneic marrow transplantation", in Biology of Bone-Marrow Transplantation, Gale and Fox, editors, Academic Press, N.Y., p.37

Thymosin alpha 1 is a compound well known in the medical field.

This compound is an acidic peptides present in thymus extract which shows immunoregulatory properties in several in vitro and in vivo assay (1972; Proc. Natl. Acad. Sci. U.S.A. 69, 1800-1803).

Previous uses of thymosin alpha 1 are already known.

WO2004087067 relates to the use of thymosin alpha 1 for preventing infection by *Aspergillus fumigatus* in an immunocompromised host being treated with a bone marrow transplantation.

Subcutaneous administration of thymosin alpha 1 to nude mice previously inoculated with human non-small cell lung cancer ("NSCLC") cells significantly decreased tumor volume.

Pulmonary metastases in mice with methylcholanthrene-induced fibrosarcoma were also reduced by thymosin alpha 1, and local sarcoma growth as well as liver and lung metastases of lymphosarcoma cells were significantly reduced in BALB/c mice treated with thymosin alpha 1.

The use of thymosin alpha 1 for preparing a medicament for the prevention or treatment of GVHD it is not known in the art.

To protect patients from GVHD, various immunosuppressive agents have been employed. Currently, allograft rejection is controlled using immunosuppressive agents such as cyclosporin A, azathioprine, corticosteroids including prednisone, and methylprednisolone, cyclophosphamide, and FK506. Cyclosporin A, the most powerful and most frequently used immunosuppressant, revolutionized the field of organ transplant surgery. Other immunosuppressive agents such as FK506, rapamycin, mycophenolic acid, 15-deoxyspergualin, mimoribine, misoprostol, OKT3 and anti-IL-2 receptor antibodies, have been used in the treatment and/or prevention of organ transplantation rejection. Briggs, Immunology letters, 29(1-2), 89-94, 1991; FASEB 3:3411, 1989. Although the development of new immunosuppressive drugs has led to substantial improvement in the survival of patients, these drugs are associated with a high incidence of side effects such as nephrotoxicity and/or hepatotoxicity.

For example, cyclosporin A has associated toxicities and side effects when used even at therapeutic doses. Although FK506 is about 10 to 100 times more potent than cyclosporin A in inhibiting activation-induced IL-2 transcription in vitro and graft rejection in vivo, it also shows side effects such as neurotoxicity and nephrotoxicity. Thus, there still exists the need for treatment and prophylaxis for GVHD with improved toxicity profiles.

SUMMARY OF THE INVENTION

It has now been found that thymosin alpha 1 is a useful agent for inhibiting or treating graft-versus-host disease or graft rejection reactions in organ transplantation in a mammal subject.

It is therefore an object of the present invention to provide the use of thymosin alpha 1 for preparing a medicament useful for the prevention or treatment of graft-versus-host disease or graft rejection reactions after organ transplantation, in a mammal subject such as a human patient which receives cells, tissue or organ(s).

A further object of the invention is to provide a method of treating or inhibiting graft-versus-host disease or graft rejection reactions in organ transplantation. The object is achieved in part by administering an effective amount of thymosin alpha 1 to a mammal requiring the same.

The cells, tissue or organ according to the present invention may be selected from the group comprising: stem cells, hematopoietic stem cells, bone marrow, heart, liver, kidney, lung, pancreas, small intestine, cornea or skin.

The thymosin alpha 1 according to the present invention may be administered in a subject which is in a myeloablative or in a non-myeloablative conditioning regimen.

The thymosin alpha 1 according to the present invention may be administered to the patient in a pharmaceutically effective amount within a predetermined time window before and/or after the transplantation, optionally in combination with an immunosuppressive agent selected from the group comprising prednisone, methylprednisolone, cyclophosphamide, cyclosporin A, FK506, thalidomide, azathioprine, Daclizumab, Infliximab, MEDI-205, abx-cbl or ATG.

The thymosin alpha 1 according to the present invention may be administered to mammal subject such as a human patient in a dose of from about 10 to 400 µg/kg body weight per day. Preferably, thymosin alpha 1 is administered in a dose of from about 40 to 400 µg/kg body weight per day. Alternatively, thymosin alpha 1 is administered in a dose of about 200 to 400 µg/kg body weight per day. The duration of the treatment will vary according to the needs of the artisan and the severity of condition being treated. Administration may be daily or less frequent and all such dosing, and administration will be apparent to those of ordinary skill without undue experimentation.

DETAILED DESCRIPTION OF THE INVENTION

The following examples further illustrate the invention.
Introduction

Thymosin alpha 1 is a naturally occurring thymic peptide (Expert Opin. Biol. Ther. 2004; 4:559-573) that promotes maturation and cytokine production in human and murine DCs by signalling, through Toll-like receptors (TLRs), including TLR9 (Blood. 2004; 103:4232-4239). By influencing the balance of IL-12- and IL-10-producing DCs, thymosin alpha 1 acts as an immune regulator capable of inducing protective immunity to *Aspergillus fumigatus* (Blood. 2004; 103:4232-4239) TLR9 stimulation can also lead to IDO activation via mechanisms including autocrine type I IFN signalling (J. Immunol. 2005; 175:5601-5605; Eur. J. Immunol. 2005; 36:8-11) and can promote pDC-mediated generation of $CD4^+CD25^+$ cells (J. Immunol. 2004; 173.4433-4442) which are an essential component of the IDO-dependent protective immunity to fungi (J. Immunol. 2005; 174:2910-2918; J. Immunol. 2006; 176:1712-1723). According to the present invention it was evaluated the activity of thymosin alpha 1 in the balance of immunity and tolerance by DCs and the generation of T reg cells. DCs were derived from bone marrow (murine) or peripheral blood (human) precursors using either GM-CSF/IL-4 (GM-DCs) or FLT3 ligand (FL-DCs), which is known to expand both conventional DCs and pDCs (J. Immunol. 2005; 174:6592-6597) with or without thymosin alpha 1. DCs were analyzed for IDO expression and ability to mediate Th1/T reg priming in vitro and in vivo against *A. fumigatus* and alloantigens. Specialization and complementarity in priming and tolerization by the different DC populations was found. However, by activating an IDO-dependent tolerogenic program via TLR9 and type I IFNR signalling, thymosin alpha 1 acted during DC differentiation to alter the balance of inflammation and tolerance.

Materials and Methods
Mice

Female, 8- to 10-wk-old inbred BALB/c and C57BL6 mice were obtained from Charles River/Harlan Breeding Laboratories (Calco, Italy). Homozygous TLR9−/− or IFN-aβR−/− mice on a C57BL6 background were bred under specific pathogen-free conditions in the Animal Facility of Perugia University, Perugia. Procedures involving animals and their care were conducted in conformity with national laws and policies.

Donors and Patients

Human peripheral blood mononuclear cells were obtained from healthy donors and seven recipients of T-cell depleted haploidentical HSCT, upon written informed consent. Donor typing, engraftment and GVHD were assessed as described (Blood. 2005; 106; 4397-4406). Experimental HSCT model Lethally irradiated (8 Gy) C57BL6 mice were infused with T cell-depleted bone marrow cells from BALB/c mice (Blood.

2003; 102:3807-3814). For GVHD, purified donor CD3+ T splenocytes were added to the graft (Science. 2002; 295: 2097-2100). Individual mice were graded weekly from 0-2 for each GVHD criterion (see legend to FIG. 3) without knowledge of treatment group.

A. fumigatus Infection

The strain of *A. fumigatus*, the culture conditions and infection were as described in Blood. 2004; 103:4232-4239. Mice were anesthetized with 2.5% avertin (Sigma Chemical Co, St. Louis, Mo.). Quantification of fungal growth in the lungs was done by the chitin assay and results are expressed as micrograms of glucosamine per pair of lungs, and PAS staining was done as described in Blood. 2004; 103:4232-4239.

Reagents

Thymosin alpha 1 and the scrambled peptide (sThymosin alpha 1) (both from SciClone Pharmaceuticals, Inc. San Mateo, Calif.) were supplied as purified, endotoxin-free sterile lyophilized acetylated polypeptides (Blood. 2004; 103: 4232-4239). The lyophilized powders were reconstituted in sterile water.

DC Subset Generation and Cultures

GM-DCs or FL-DCs were obtained from purified CD14+ monocytes from healthy donors or transplanted patients (1 month post-HSCT) cultured in Iscove's modified medium for 7-9 days, in the presence of rGM-CSF (Schering-Plough, Milan, Italy) and rIL-4 (Peprotech, Inalco, Milan, Italy) or FLT3-L (Immunex Corporation, Seattle, Wash.) (Blood. 2004; 103:4232-4239). DC recovery was between 20-30% reduced in cultures from transplanted patients. Murine GM-DCs or FL-DCs were obtained from bone marrow cells for 7-9 days, as described (Blood. 2004; 103:4232-4239). Thymosin alpha 1 and sThymosin alpha 1 were added to the cultures at 20 ng/mL. DCs (>99% CD11c+ consisting of 90-95% CD8−, 5-10% CD8+, and 1-5% B220+ cells) were purified from spleens (spDCs) by magnetic-activated sorting using CD11c MicroBeads and MidiMacs (Miltenyi Biotech). DC populations were further separated into CD8−, CD8+ and B220+ fractions by means of CD8 or B220 MicroBeads (Miltenyi Biotech). DCs were pulsed in serum-free Iscove medium for 24 hours with live unopsonized *Aspergillus* conidia or Zymosan from *Saccharomyces cerevisiae* (Sigma) or CpG-ODN 2006 as described.7 Phagocytosis was done as described (Blood. 2004; 103:4232-4239). Photographs were taken using a high Resolution Microscopy Color Camera AxioCam, using the AxioVision Software Rel. 3.1 (Carl Zeiss, Milan, Italy).

Flow Cytometry

DCs were analyzed for antigen expression with a FACScan flow cytofluorometer (Becton Dickinson, Mountain View, Calif.) equipped with CELLQuest™ software and using conjugated mAbs from PharMingen (Blood. 2004; 103:4232-4239).

IDO Expression and Functional Analysis

IDO expression and functional activity were assessed as described in Nat. Immunol. 2002; 3:1097-1101. Generation, purification and activity of T reg cells Splenic CD4+ T-cells were cocultured with conidia-pulsed DCs for 5 days 7 before flow cytometry or ELISPOT assay. 1-MT (Sigma-Aldrich) was used at 2 µM. CD4+CD25+ and CD4+CD25− cells (>90% pure on FACS analysis) were separated by magnetic cell sorting from lung and TLN (J. Immunol. 2006; 176:1712-1723). For T reg cell inhibition, $5\times10^4$ TLN T reg cells were added to $3\times10^5$ CD4+CD25− cells, both from transplanted mice, stimulated with $3\times10^4$ autologous *Aspergillus* conidia-pulsed spDCs or with or $1.5\times10^5$ allogeneic spDCs from naïve donor mice for five days before $H^3$-thymidine labeling. Purified peritoneal CD 11b+Gr−1+PMN (>98% pure on FACS analysis) ($2\times10^6$) were exposed to resting conidia in the presence of $4\times10^5$ CD4+CD25+ for 60 min for oxidant production or 24 hours for cytokine production (J. Immunol. 2006; 176:1712-1723).

Cytokine and ELISPOT Assay

Cytokine content was assessed by enzyme-linked immunosorbent assays (Endogen Human Elisa Kits, R&D Systems and Euroclone, Milan, Italy). AID EliSpot assay kits (Amplimedical, Buttigliera Alta, Turin, Italy) were used on purified splenic CD4+ T cells cocultured with conidia-pulsed DCs for 5 days to enumerate cytokine-producing cells (Blood. 2003; 102:3807-3814). 1-MT was used at 2 µM.

Adoptive Transfer, Fungal Challenge, and Assessment of Protection

Mice received twice intraperitoneal injections of DCs, at weekly interval, starting a day after HSCT and infected a week after the last DC administration. Three days later, lung homogenates, CD4+ T cells (>98% on FACS analysis), CD4+CD25− (>98%) or CD4+CD25+ (>82%) purified with the specific Miltenyi Biotec isolation kits were assessed for pattern of pro- and anti-inflammatory (TNF-a/IL-10 in lung homogenates), Th1 (IFN-γ) or Th2 (IL-4) cytokine production by CD4+ cells stimulated with *Aspergillus*-pulsed DCs (Blood. 2003; 102:3807-3814) frequency of CD25+ IL-10+ TGF-β+ T reg cells, lymphoproliferation and gene expression by RT-PCR. For proliferation, TLN CD4+ T lymphocytes were plated ($10^5$ cells/well) with $10^5$ cells/well irradiated allogeneic splenocytes or autologous spDCs pulsed with conidia or 10 µg/mL Con A for five days before $H^3$-thymidine labeling.

Generation of *Aspergillus*-Specific Human T Cell Clones and Lymphoproliferation

*Aspergillus*-specific human CD4+ T cell clones were generated from peripheral blood CD4+CD45RA+ T cells added at limiting dilution concentrations to irradiated (20 Gy) feeder autologous peripheral blood cells and stimulated with conidia-pulsed DCs or allogeneic DCs (Blood. 2005; 106: 4397-4406). Growing clones were assessed for specificity against fungus-pulsed DCs, allogeneic DCs, autologous irradiated cells (as a negative control) and 0.5% phytohemoagglutinin (as a positive control) by $H^3$-thymidine (Amersham Biosciences, Little Chalfont, UK) labeling or cytokine content in supernatants 2 days later (Blood. 2005; 106:4397-4406).

Reverse Transcriptase (RT)-PCR

RNA extraction, synthesis and PCR of cDNA, sequences of gene-specific primers, annealing temperatures and amplification cycles were done as described in J. Immunol. 2006; 176:1712-1723). Amplification efficiencies were validated and normalized against GAPDH.

Statistical Analysis

Student's paired t test was used to determine the significance of values in experimental groups (significance was defined as P<0.05). Survival data were analyzed using the Mann-Whitney U test. In vivo groups consisted of 6 animals.

EXAMPLE 1

Thymosin Alpha 1 Expands pDCs from Bone Marrow Precursors and Activates Tryptophan Catabolism To assess how Thymosin alpha 1 would affect the phenotypic and functional properties of murine DCs, bone marrow cells were grown for 7-9 days in medium containing GM-CSF/IL4 or FLT3L, in the presence of Thymosin alpha 1 or a control, scrambled peptide. After maturation, cells were analyzed by flow cytometry and light microscopy (FIG. 1A). Contrary to FLT3L, GM-CSF/IL-4 treatment alone would not allow for the emergence of a high fraction of pDCs, as revealed by the percentage of B220+CD11c+cells on FACS analysis and by morphology examination using light microscopy. However, Thymosin alpha 1, which did not affect total yield of cells greatly increased the occurrence of pDCs in GM-DCs, as revealed by a higher number of B220+CD11c+ DCs and a slightly decreased recovery of conventional CD11b+CD11c+ cells.

Although Thymosin alpha 1 is known to affect hematopoiesis, expansion of B220+CD11c+ cells was not observed with Thymosin alpha 1 alone. B220+CD 11c+ cells were not increased in FL-DCs treated with Thymosin alpha 1 nor were they in GM-DCs treated with the control peptide. Expansion of pDCs by Thymosin alpha 1 was not observed in GM-DCs from TLR9−/− or IFN-aβR−/−mice, indicating dependency of Thymosin alpha 1 effects on TLR9 and type I IFNR signaling.

EXAMPLE 2

Thymosin Alpha 1 Promotes the Induction of IL-12 by Myeloid DCs and of IL-10 by pDCs.16

Thymosin alpha 1 induced release of IL-12 and IL-10 by GM-DCs in response to *Aspergillus conidia* and of IL-10, more than IL-12, by FL-DCs (FIG. 1B). Production of IL-10 by DCs in response to fungi is regulated by an IDO-dependent pathway (J. Immunol. 2005; 174:2910-2918); In the current setting, IL-10 production by either population in response to Thymosin alpha 1 did not occur with cells from TLR9−/− or IFN-aβR−/−mice, and was likewise blocked by the addition of the IDO inhibitor 1-methyl-DL-tryptophan (1-MT) to the cultures (FIG. 1B). Induction of functional IDO by Thymosin alpha 1 in both FL-DCs and GM-DCs was confirmed by immunoblot analysis and by assessment of enzymic activity in terms of DC conversion of tryptophan to kynurenine. Again, induction of IDO protein and function by Thymosin alpha 1 was not observed in DCs from TLR9−/− or IFN-aβR−/−mice (FIG. 1C).

EXAMPLE 3

Thymosin Alpha 1-Induced, IDO+ DCs Activate T Reg Cells In Vitro

To correlate IDO expression and IL-10 production by DCs with possible regulatory activities, we examined the relative ability of Thymosin alpha 1-induced DCs to induce antigenspecific Th1/T reg priming in vitro by splenic CD4+ T lymphocytes in response to *Aspergillus conidia*. FIG. 2A shows that Thymosin alpha 1 increased priming for IFN-γ-/IL-10producing CD4+ T cells by GM-DCs and for IL-10-producing cells by FL-DCs. Similar to IDO blockade, depletion of B220+CD11c+ from Thymosin alpha 1-GM-DCs abolished Treg cell activation (data not shown). IDO blockade by 1-MT prevented activation of the IL-10-producing CD4+ cells but had no effect on IFN-γ-producing cells, suggesting that IDO is causally and selectively linked to priming for IL-10-producing T cells. Because TLR9 stimulation activates IDO (J. Immunol. 2005; 175:5601-5605) and also promotes pDCmediated generation of CD4+CD25+ T reg cells (J. Immunol. 2004; 173:4433-4442) the occurrence of CD4+ CD25+ T cells expressing markers of T reg activity, such as the forkhead transcription factor Foxp3 and cytotoxic T lymphocyte antigen 4 (CTLA-4). Cytofluorimetric analysis revealed that CD4+CD25+ T cells were expanded by coculture with DCs (FIG. 2B). However, a significant proportion of the CD4+CD25+ T cells stained positive for intracellular Foxp3 and surface CTLA-4 when cultured in the presence of Thymosin alpha 1-induced DCs. The effect was negated by IDO blockade. FL-DCs also induced Foxp3+ T reg cells, although to a lesser degree. In accordance with the data in FIG. 1C suggesting that tryptophan catabolism is enhanced by FLT3L, 1-MT appeared to interfere with the expansion of Foxp3+CTLA4+CD25+ T cells co-cultured with FL-DCs. Therefore, the development of CD4+CD25+ T reg cells in vitro seemingly occurs through a mechanism involving DC tryptophan catabolism and is promoted by Thymosin alpha 1.

EXAMPLE 4

Thymosin Alpha 1-Conditioned GM-DCs Protect Hosts from Aspergillosis in HSCT

Fungus-pulsed DCs act as a potent fungal vaccine in experimental HSCT.7 Because regulation is absolutely required to balance inflammation and tolerance in HSCT24, 25 as well as in antifungal immunity (J. Immunol. 2005; 174:2910-2918).

It was examined whether Thymosin alpha 1-treated DCs would affect priming and tolerization in vivo in an experimental setting of HSCT. Transplanted mice were infused with fungus-pulsed DCs, infected with *Aspergillus conidia* and monitored for survival, fungal growth and inflammatory pathology in the lungs. Similar to splenic DCs,7 FL-DCs but not GM-DCs conferred resistance to infection in a dose-dependent manner, as mice survived infection and controlled fungal growth after transfer of $5 \times 10^5$ (FIG. 3A) but not $5 \times 10^4$ DCs. A paradoxical effect was observed in mice treated with GM-DCs in that mice failed survive challenge in spite of their effective control of fungal growth. However, Thymosin alpha 1 treatment, which would not affect the vaccinating potential of FL-DCs, dramatically increased that of GM-DCs, as shown by the complete protection afforded by transfer of Thymosin alpha 1-treated GM-DCs (FIG. 3A). FL-DCs encompass populations equivalent to mixtures of freshly harvested splenic CD8+, CD8− and B220+LyC6+ pDCs.20 To dissect the contributions of different subsets to the vaccinating potential of DCs, fractions purified from FL-DC or splenic populations were examined, alone or in combination, for ability to induce protection to aspergillosis in HSCT. The results showed that neither CD8− nor CD8+ DCs alone conferred resistance to infection, as judged by extensive fungal growth and dissemination. However, protection was observed on combining the two subsets and was similar to that observed with pDCs purified from either the spleen or FL-DC cultures (data not shown). Therefore, the combination of functionally distinct activities was likely responsible for the protective action in vivo of FL-DCs and Thymosin alpha 1treated GM-DCs in the experimental setting of aspergillosis in HSCT.

EXAMPLE 5

Thymosin Alpha 1 Conditioning of GM-DCs Generates an Immune Component Blunting Immunotoxicity Histopathology revealed that local inflammatory cell recruitment and reaction were high in the lungs of GM-DC-treated mice but low in mice infused with Thymosin alpha 1-treated GM-DCs or with FL-DCs (FIG. 3B). These findings suggested that a severe inflammatory toxicity was likely associated with the transfer GM-DCs, an effect alleviated by Thymosin alpha 1 pre-conditioning of the GM-DCs. To directly unmask the potential for immunotoxicity of DCs, and its taming by Thymosin alpha 1, the different DC populations were infused into mice receiving different numbers of donor T cells along with the graft.

Mice were either left uninfected for the assessment of GVHD or infected for the assessment of susceptibility to infection. Although the initiation of GVHD after stem cell transplantation is dependent on direct antigen presentation by host APCs (Science. 1999; 285:412-415; Nat Med. 2004; 10:510-517) the indirect antigen presentation by donor APCs has also been described (Nat Med. 2004; 10:987-992). In line with previous findings (Science. 2002; 295:2097-2100) the severity of GVHD was dependent on the number of infused T cells, signs of GVHD being observed within 10 and 30 days after the respective infusion of $5 \times 10^5$ or $1 \times 10^5$ T cells. The co-administration of GM-DCs greatly accelerated the induction of GVHD by $10^5$ T cells but, similar to FL-DCs, Thymosin alpha 1-treated GM-DCs totally prevented the effect (FIG. 3C). In terms of susceptibility to infection, survival was not modified after the infusion of donor T cells either alone or along with GM-DCs. In contrast, similar to mice given FL-DCs, mice infused with Thymosin alpha 1-treated GM-DCs survived infection (FIG. 3D). Together, these results suggested that, like spDCs, FL-DCs are fully competent at inducing antifungal protection after adoptive transfer in HSCT recipients. In contrast, GM-DCs are endowed with immunotoxicity, including the promotion of inflammation and GVHD, an activity in the host amenable to regulatory effects initiated by Thymosin alpha 1 in vitro.

EXAMPLE 6

Thymosin Alpha 1-Induced DCs Prime for Antifungal Th1/T Reg Responses

To determine whether Thymosin alpha 1-treated DCs will induce T reg cells in vivo, were assessed the levels of TNF-a/IL-10 production in lung homogenates, IFN-γ/IL-4 production by TLN CD4+ T cells, and expression of the genes coding for IFN-γ, the Th2-specific transcription factor GATA-3 and Foxp3 in TLN CD4+ T cells. Were also assessed the presence of CD4+CD25+ T cells in the lungs and TLN, as functionally distinct T reg populations are found in the lungs and TLN of mice with aspergillosis J. Immunol. 2006; 176: 1712-1723). The results showed disparate patterns of TNF-a/IL-10 production in the different groups. TNF-a was high and IL-10 was low in mice either untreated or infused with GM-DCs, the reverse being true in mice receiving FL-DCs and particularly Thymosin alpha 1-treated GM-DCs (FIG. 4A). The assessment of the actual IFN-γ/IL-4 production by CD4+ T cells revealed that the amount of IFN-γ was higher and that of IL-4 lower in mice given Thymosin alpha 1-treated GM-DCs or given FL-DCs irrespective of their treatment (FIG. 4A). PCR analysis showed that IFN-γ mRNA expression was always present; Gata3 mRNA was detected in mice either untreated or treated with FL-DCs unexposed to Thymosin alpha 1, and Foxp3 mRNA was expressed in mice given FL-DCs, irrespective of Thymosin alpha 1 exposure, or given Thymosin alpha 1-treated GM-DCs (FIG. 4B). Levels of glucocorticoid inducible TNF receptor (GITR) expression were assessed and were found to be broadly expressed, with no significant differences among experimental groups. Cytofluorimetric analysis revealed that the number of CD4+CD25+ T cells increased in TLN and lungs of mice infused with any type of DC, whether untreated or treated with Thymosin alpha 1 (FIG. 4C). Interestingly, some sort of differential compartmentalization was observed in that Thymosin alpha 1 treated GM-DCs induced T reg in the lungs more than TLN and the opposite was true for Thymosin alpha 1-treated FL-DCs. CD4+CD25+ T cells recov ered from mice given Thymosin alpha 1-treated GM-DCs or FL-DCs did not stain positive for the CD69 activation marker, as observed with cells recovered from mice given untreated GM-DCs (FIG. 4C). Consistent with the notion that the migration and occupancy of draining lymph nodes is required for graft acceptance,29 CD25+ T cells recovered from mice given FL-DCs or Thymosin alpha 1-treated GM-DCs also stained positive for the CD62L marker. TLN T reg cells contained high numbers of IL-10- or TGF-β-producing cells (FIG. 4A), while lung T reg cells contained more IL-10- than TGF-β-producing cells.

Altogether, these results suggested that GM-DCs exposed to Thymosin alpha 1 convert an inflammatory/Th1 response to a protective Th1/T reg response upon adoptive transfer in vivo. However, the finding that induced T reg cells home to different compartments could be related to possible phenotypic and functional differences between the different T reg populations. This would be consistent with the finding that a division of labor occurs between the functionally distinct T reg populations that are coordinately activated in the lungs and TLN of mice exposed to *Aspergillus* (J. Immunol. 2006; 176:1712-1723). Alternatively, after a first level of activation and priming in lymph nodes by cognate recognition, activated T reg cells may become effector T reg cells capable of trafficking to infected tissues where they control the local inflammatory response.

EXAMPLE 7

Antifungal T Reg Cells Inhibit Alloreactivity and Inflammation

Figure 5:
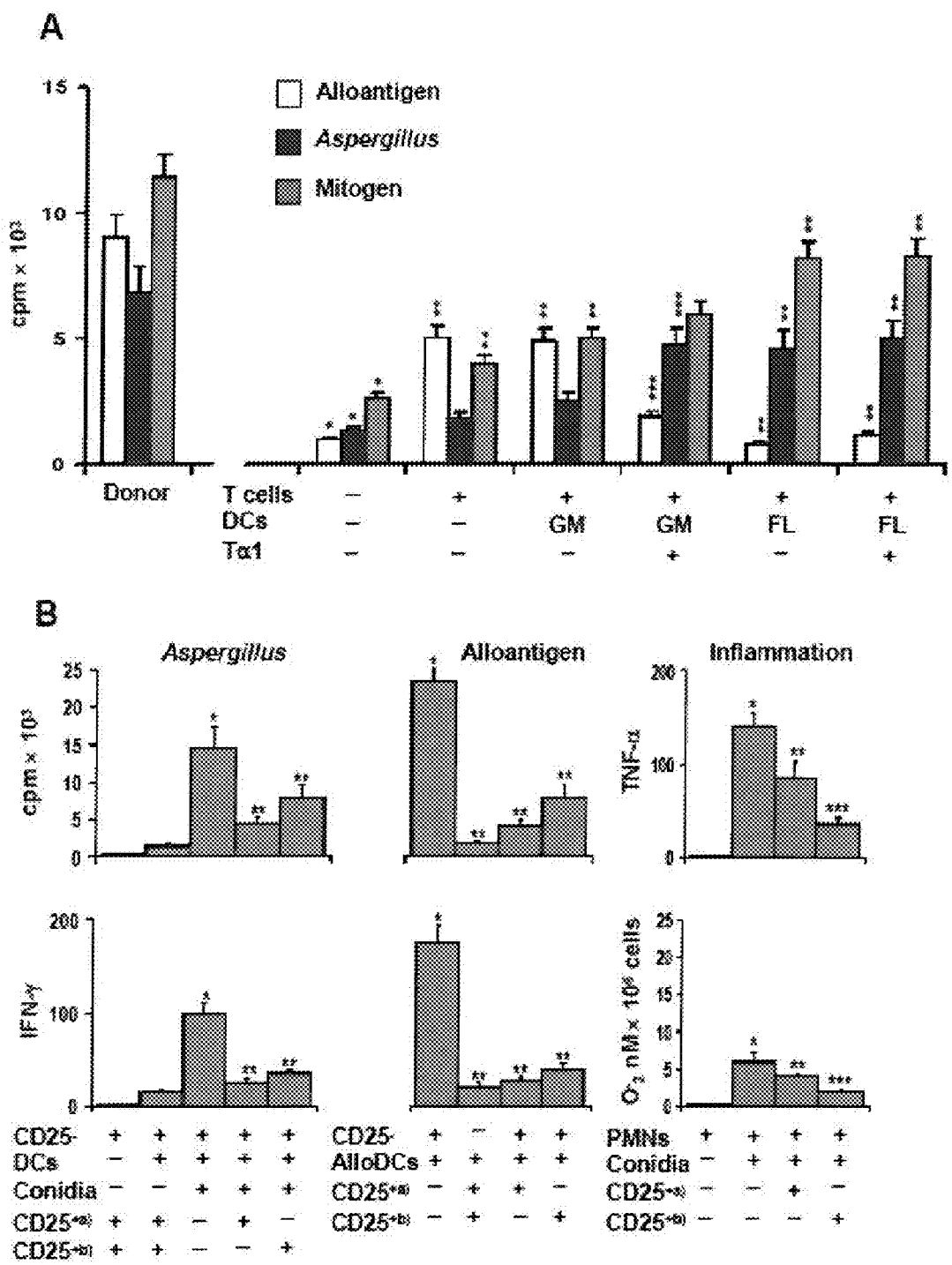

To assess the suppressive activity of CD25+ T reg cells, TLN cells from mice given the different DC subsets were assessed for proliferative response to allogeneic splenocytes, *Aspergillus conidia* or mitogen. The results showed that allogeneic, but not *Aspergillus*-specific, proliferation was observed in mice receiving T cells alone or together with GM-DCs. In contrast, alloreactivity decreased but pathogen-specific reactivity recovered in mice receiving FL-DCs or Thymosin alpha 1-treated GM-DCs, although to a lower degree compared to that of donor controls (FIG. 5A). As the response to mitogen was comparable among DC-treated mice, these results suggested that T reg cells directly impact on both allogeneic and pathogen-specific Th1 reactivity. To clarify this issue, purified CD4+CD25+ T cells from TLN were assessed for ability to block the *Aspergillus*- or alloantigen-specific proliferation of, and IFN-γ production by, the corresponding CD4+CD25− T cells. While CD4+CD25+ T cells were hyporesponsive to alloantigens and *Aspergillus*, alloreactivity and the antigen-specific responses were both reduced in the presence of CD4+CD25+ T cells from mice receiving FL-DCs or Thymosin alpha 1-treated GM-DCs (FIG. 5B). As lung T reg cells are endowed with potent anti-inflammatory activity in pulmonary aspergillosis (J. Immunol. 2006; 176:1712-1723), the suppressive activity of lung CD4+CD25+ T cells on the antifungal effector activity of neutrophils, such as TNF-a and oxidant production, was also examined because these functions are exquisitely sensitive to the suppressive activity of T reg cells (J. Immunol. 2006; 176:1712-1723). Both functions were significantly inhibited by lung T reg cells and, particularly, by the T reg fraction induced by Thymosin alpha 1-treated GM-DCs (FIG. 5B).

EXAMPLE 8

Thymosin Alpha 1 Promotes Mobilization and Th1/T Reg Antifungal Priming of Human DCs To assess whether Thymosin alpha 1 may affect the Th1/T reg priming potential of human DCs, GM- or FL-DCs were derived from peripheral CD14+ cells from healthy donors in the presence of Thymosin alpha 1. As with murine DC cultures, Thymosin alpha 1 promoted the mobilization of CD123+ pDCs while decreasing that of CD1a+DCs in GM-CSF/IL-4-treated cultures.

Figure 6:
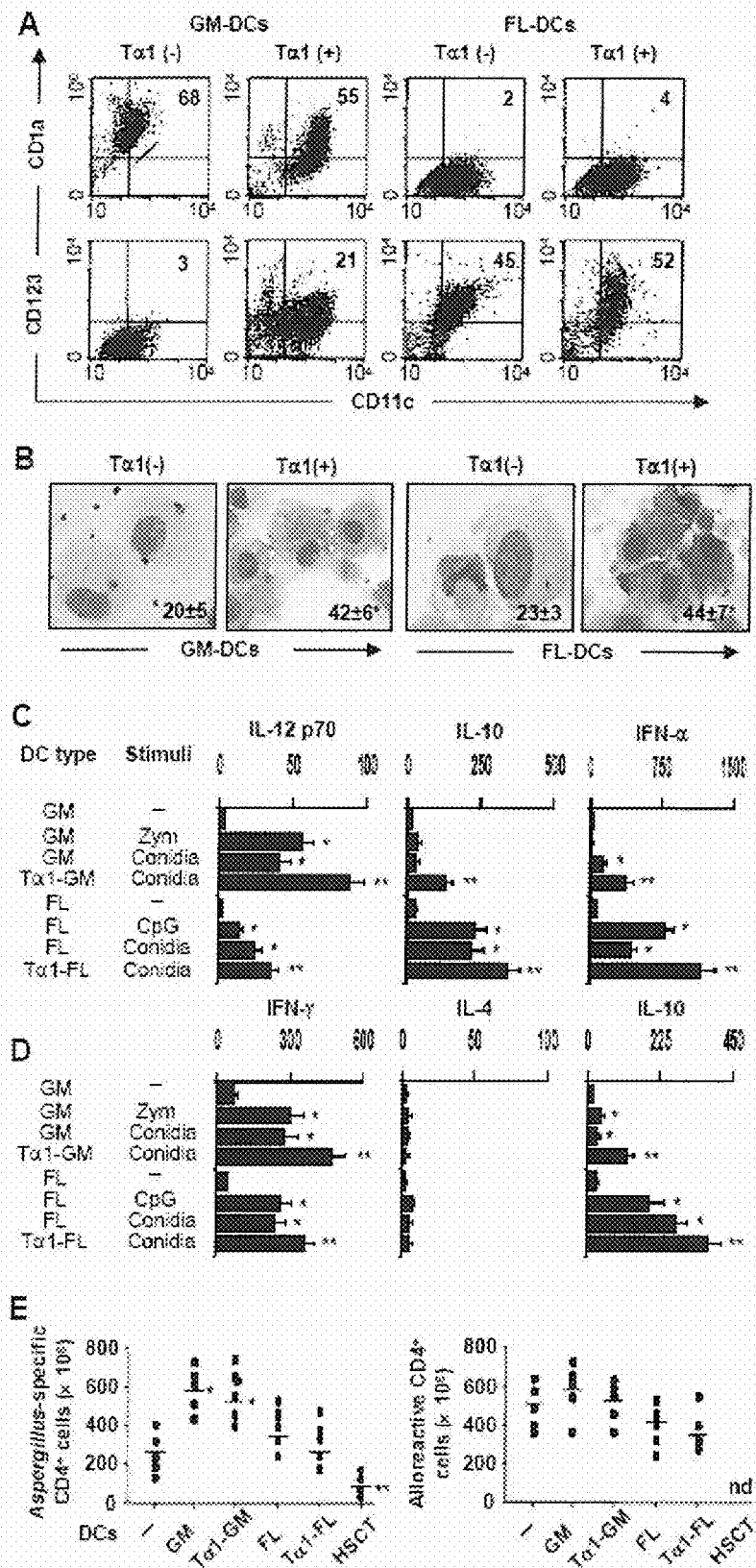

No such effects were observed in FLT3-L cultures (FIG. 6A). Thymosin alpha 1 significantly modified the microbial sensing of GM-DCs or FL-DCs in terms of phagocytosis (from 30 to 56% phagocytosis in GM-DCs and from 32 to 58% phagocytosis in FL-DCs). Interestingly, however, Thymosin alpha 1 also promoted the phagocytosis of both GM- and FL-DCs derived from patients one month after transplantation (FIG. 6B). In terms of functional activity, Thymosin alpha 1 converted inflammatory IL-12-producing GM-DCs into tolerogenic pDCs that, similar to FL-DCs, produced increased levels of IL-10 (FIG. 6C) and primed for IL-10-producing CD4+ T cells in vitro (FIG. 6D). As type I IFNs-producing pDCs are known to participate in the induction and maintenance of tolerance as well as in the tolerogenic effects of Thymosin alpha 1, the production of IFN-a in response to *Aspergillus conidia* or Zymosan (meant to be a positive control for GM-DCs) or CpG ODN (a positive control for FL-DCs) was also compared. IFN-a was mainly produced by FL-DCs or Thymosin alpha 1-treated GM-DCs (FIG. 6C). Finally, was examined whether Thymosin alpha 1 treatment would modify the ability of DCs to activate fungus- or alloantigen-specific T cell reactivity. FIG. 6E shows that Thymosin alpha 1 modified neither the antigen-specific T cell responses induced by DCs nor the allostimulatory capacity of whichever type of DC. As a matter of fact, induction of fungus-specific T cell reactivity was totally absent in DCs from transplanted patients. These data indicate therefore that Thymosin alpha 1, by harnessing inflammatory DCs, may meet the requirements for successful antifungal Th1/T reg cell priming in the absence of alloreactivity in hematopoietic transplantation.

The results obtained, reported in the examples above mentioned, shown that Thymosin alpha 1 expands a pDC fraction in GM-DCs that is competent for IDO function and that IDO+pDCs are necessary and sufficient to mediate antimicrobial immunity and alloantigen tolerization in experimental HSCT.

This is the demonstration that Thymosin alpha 1 act as a natural hormone contributing to the induction and maintenance of peripheral tolerance in physiology and paraphysiology status.

The present invention contemplates a therapeutic package for dispensing to, or for use in dispensing to, a patient being treated for the prevention or treatment of graft-versus-host disease or graft rejection reactions in organ transplantation, comprising one or more unit doses, each unit dose comprising an amount of thymosin alpha 1, and optionally an amount of an immunosuppressive agent.

The present invention contemplates an article of manufacture comprising packaging material and thymosin alpha 1, and optionally an immunosuppressive agent, contained within said packaging material, wherein the thymosin alpha 1 is therapeutically effective for the prevention or treatment of graft-versus-host disease or graft rejection reactions in organ transplantation, and wherein the packaging material comprises a label which indicates that thymosin alpha 1 can be used for the prevention or treatment of graft-versus-host disease or graft rejection reactions in organ transplantation.

According to the present invention thymosin alpha 1 and optionally the immunosuppressive agent can be administered in a separate form or in the form of a unitary dosage comprising the active ingredients and optionally diluent or excipients pharmaceutically acceptable.

According to the present invention when thymosin alpha 1 and the immunosuppressive agent are administered in a separate form (i.e. 2 different administration), said active ingredients may be administered sequentially (i.e. in the same moment) or sequentially according to a schedule suggested in the labeling above mentioned.

In the use according to the invention, the terms "treat" or "treating" bear their usual meaning which includes preventing, prohibiting, alleviating, inhibiting, ameliorating, halting, restraining, slowing or reversing the progression, activation or reduction of the severity of the GVHD.

In the use according to the invention, the term "effective amount" refers to an amount of the compound, which is capable of performing the intended result. For example, an effective amount of thymosin alpha 1, and optionally the immunosuppressive agent that is administered in an effort to treat the GVHD is that amount which is required to prevent, prohibit, alleviate, ameliorate, halt, restrain, slow or reverse the progression, or reduce the severity of said GVHD, and the daily dose to be administered will depend, according to the judgement of the primary care physician, on the subject's weight, age and general condition of the patient.

In those aspects of the invention where the thymosin alpha 1 is administered to treat or inhibit graft-versus-host disease or graft rejection reactions in organ transplantation in a mammal the dose of thymosin alpha 1 is in one aspect from about 10 to 400 pg/kg body weight per day. Preferably, the dose is from about 40 to 400 pg/kg body weight per day. Alternatively, the dose is from about 200 to 400 pg/kg body weight per day. While any route of administration can be used, one preferred route is to give the thymosin alpha via subcutaneous injection. One preferred source of thymosin alpha 1 is Zadaxin® available from SciClone Pharmaceuticals of San Mateo, Calif. See also, the package insert for Zadaxin®, the contents of which are incorporated herein by reference.

The duration of the treatment will vary according to the needs of the artisan and the severity of condition being treated. Administration may be daily or less frequent and all such dosing, and administration will be apparent to those of ordinary skill without undue experimentation. In one aspect of the invention the dosing frequency is once every two weeks. In another aspect, the dosing is weekly, or more frequently, as determined from clinical assessment. Less frequent dosing, of course, is also contemplated herein.

In an alternative aspect of the invention, thymosin alpha 1 is administered in a dose of from about 0.8 to 16 mg per day. Preferably, thymosin alpha 1 is administered in a dose of from about 0.8 to 6.4 mg per day. Alternatively, thymosin alpha 1 is administered in a dose of from about 1.4 to 2.8 mg per day. More preferably, thymosin alpha 1 is administered in a dose of about 1.6 mg per day. The same dosing frequency described above can be used.

As discussed above, thymosin alpha 1 can be administered via subcutaneous injection.

The present invention also includes methods employing pharmaceutical formulations, which contain, as the active ingredient, thymosin alpha 1, and optionally an immunosuppressive agent, in association with pharmaceutical carriers. A skilled artisan would know of such formulations and their manufacture, see, e.g., REMINGTON'S PHARMACEUTICAL SCIENCES, (16th ed. 1980).

The formulations may be prepared in a unit dosage form of the active ingredient. The term "unit dosage form" refers to physically discrete units suitable as unitary dosages for human subjects, each unit containing a predetermined quantity of thymosin alpha 1, and optionally the immunosuppressive agent, calculated to produce the desired therapeutic effect, in association with a suitable pharmaceutical excipient.

Thymosin alpha 1, and optionally the immunosuppressive agent can be administered in the form of a pharmaceutical composition in combination with pharmaceutically acceptable carriers or excipients, the proportion and nature of which are determined by the solubility and chemical properties of the compound in the carriers and/or excipients selected, the chosen route of administration, and standard pharmaceutical practice.

Pharmaceutical compositions are prepared in a manner well known in the pharmaceutical art see, e.g., REMINGTON'S PHARMACEUTICAL SCIENCES, (16th ed. 1980).

The carrier or excipient may be a solid, semi-solid, or liquid material, which can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solution, suspensions, liposome or the like.

DISCUSSION OF THE DRAWINGS

Figure 1A:
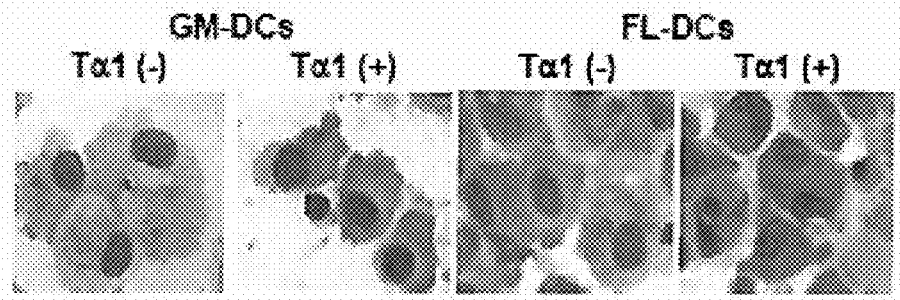

FIG. 1
Thymosin Alpha 1 Expands pDCs from Bone Marrow Precursors and Activates Tryptophan Catabolism (A) Surface expression of CD11c, CD 11b and B220 on DCs derived from bone marrow of C57BL6, TLR9−/− or IFN-aβR−/−mice and cultured with GM-CSF/IL-4 (GM-DCs) or FLT3L (FL-DCs) in the presence of Thymosin alpha 1 (+) or the scrambled peptide ( ). Percent of double positive cells is indicated.

(B) Cytokine production (ELISA) by GM-DCs or FL-DCs cultured in serum-free medium ($1 \times 10^6$ cells/mL) with unopsonized Aspergillus conidia ($5 \times 10^5$/mL) for 24 hours. The IDO inhibitor 1-MT was added at 2 µM. Data are aggregated results from three independent experiments. The detection limits (pg/mL) of the assays were <16 for IL-12p70 and <12 for IL-10.

(C) Increased IDO function and expression in DCs derived as in (A). Cells were assessed for IDO protein expression by immunoblotting and for kynurenine production. Positive and negative controls consisted of IDO protein-expressing MC24 transfectants and mock-transfected MC22 cells, respectively (not shown in the figure).

Data are means±SE of triplicate samples in one experiment representative of three.

Figure 2:
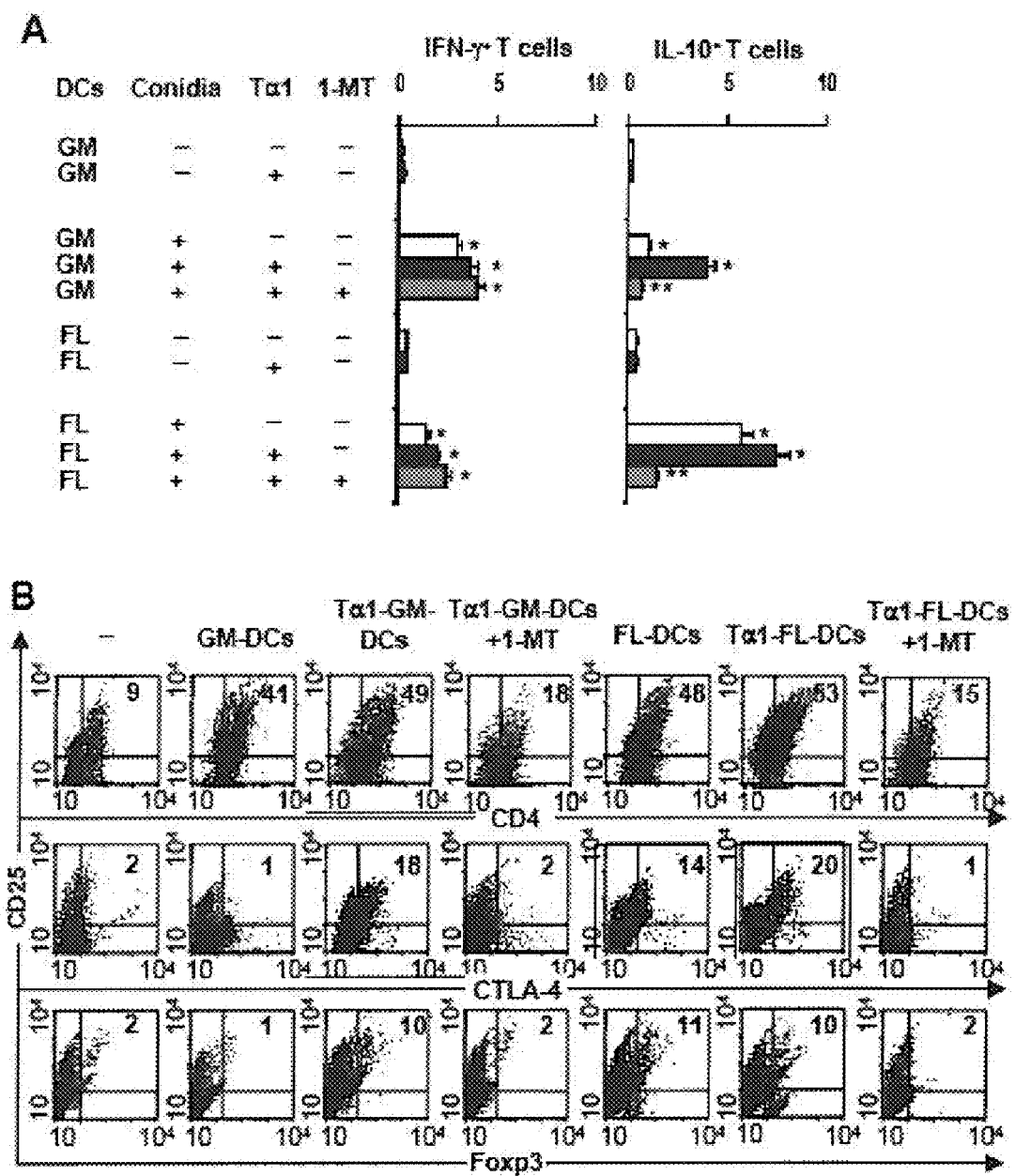

FIG. 2
Thymosin Alpha 1-Induced, IDO+ DCs Activate T Reg Cells In Vitro (A) Frequency of IFN-γ-/IL-10-producing splenic CD4+ T cells activated by Aspergillus-pulsed Thymosin alpha 1-treated GM-DCs or FL-DCs. 1-MT was present in selected cultures. Plates were read with the AID-EliSpot Reader System (Amplimedical). Values are means±SE per $10^6$ cells of samples from 3-5 experiments, calculated using replicates of serial twofold dilutions of cells. (*) $P<0.05$, conidia-exposed versus unexposed cells; (**) $P<0.05$, thymosin-exposed versus unexposed cells.

(B) Phenotypic analysis of CD4+ cells cultured alone (−) or as in (A). Numbers represent the percentage of double positive cells.

Figure 3:
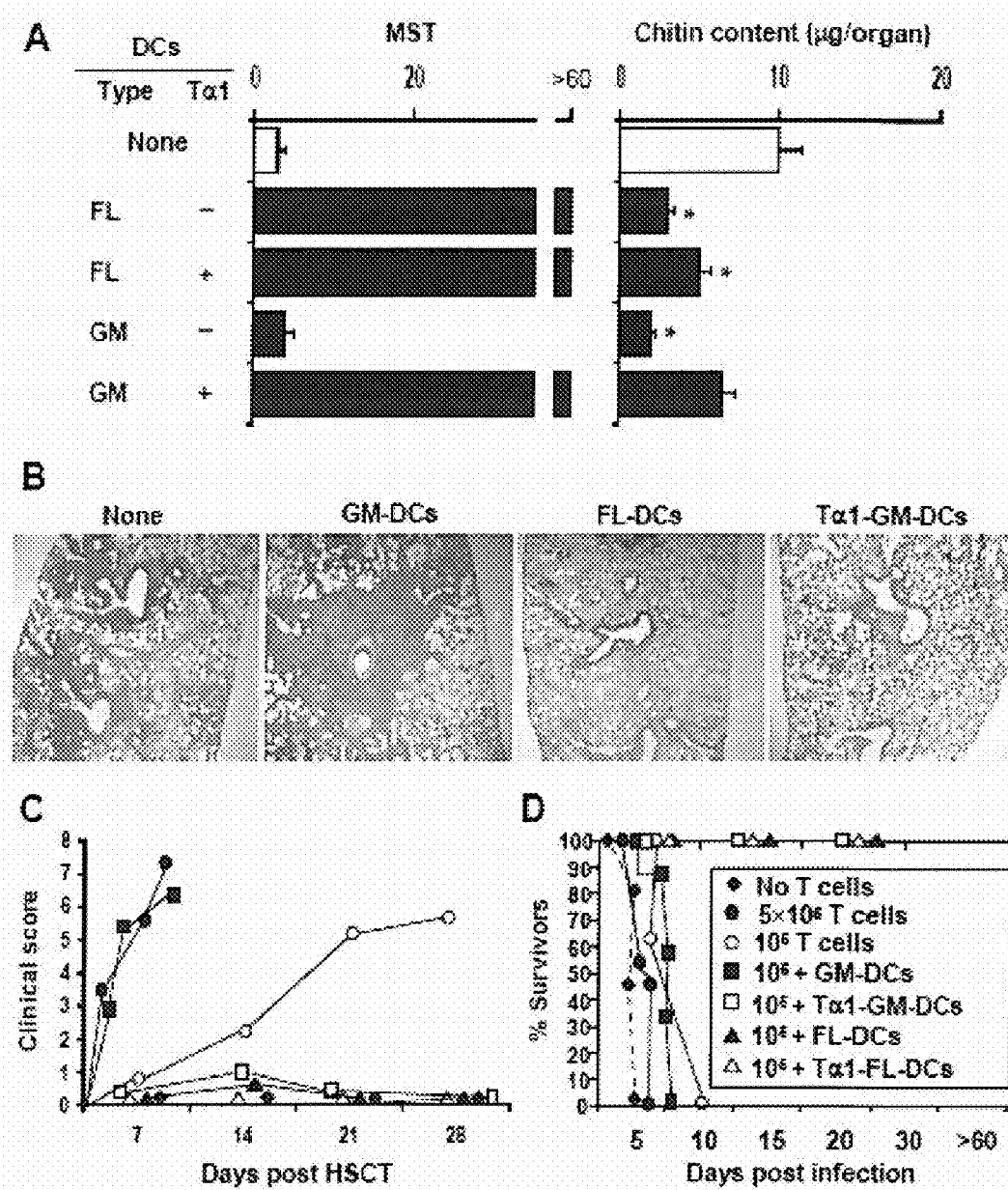

FIG. 3
Thymosin Alpha 1-Treated DCs Protect from Aspergillosis in Experimental HSCT Lethally irradiated C57BL/6 mice received=$2 \times 10^6$ T cell-depleted allogeneic bone marrow cells from BALB/c mice 2 wk before the intratracheal injection of $2 \times 10^8$/80 µl saline Aspergillus conidia. One and seven days after transplantation, mice received Aspergillus-pulsed GM- or FL-DCs grown in Thymosin alpha 1, intraperitoneally.

Resistance to infection was assessed in terms of MST (median survival time in days) and fungal growth in the lung (pg/organ glucosamine content, bars indicating standard errors) 3 days after infection or at the time of death (A). Also shown in figure are inflammatory lung pathology (B), occurrence of GVHD reactivity (C) and susceptibility to infection (D) in the presence of donor T cells. (B) Periodic acid-Schiff-stained sections were prepared from lungs of mice infected with Aspergillus conidia 3 days earlier either untreated (None) or receiving different types of DCs. Severe signs of bronchial wall damage and necrosis and scarce inflammatory cell recruitment were observed in the lungs of untreated or GM-DC-treated mice, as opposed to mice receiving Thymosin alpha 1-treated GM-DCs or FL-DCs, whose lungs were characterized by few healing infiltrates of inflammatory cells with no evidence of bronchial wall damage and inflammatory response. Magnification×200. (*) $P<0.05$, mice receiving DCs vs untreated mice. (C) Pathology scores for representative mice receiving, with the graft, different numbers of donor T cells alone or together with different DC types. The degree of systemic GVHD was assessed by a scoring system that sums changes in five clinical parameters: weight loss, posture (hunching), activity, fur texture, and skin integrity (maximum index=10). (*) $P<0.05$, mice receiving T cells+Thymosin alpha 1-GM-DCs versus T cells+untreated GM-DCs. (D) Survival to infection in mice treated as in (C).

Figure 4:
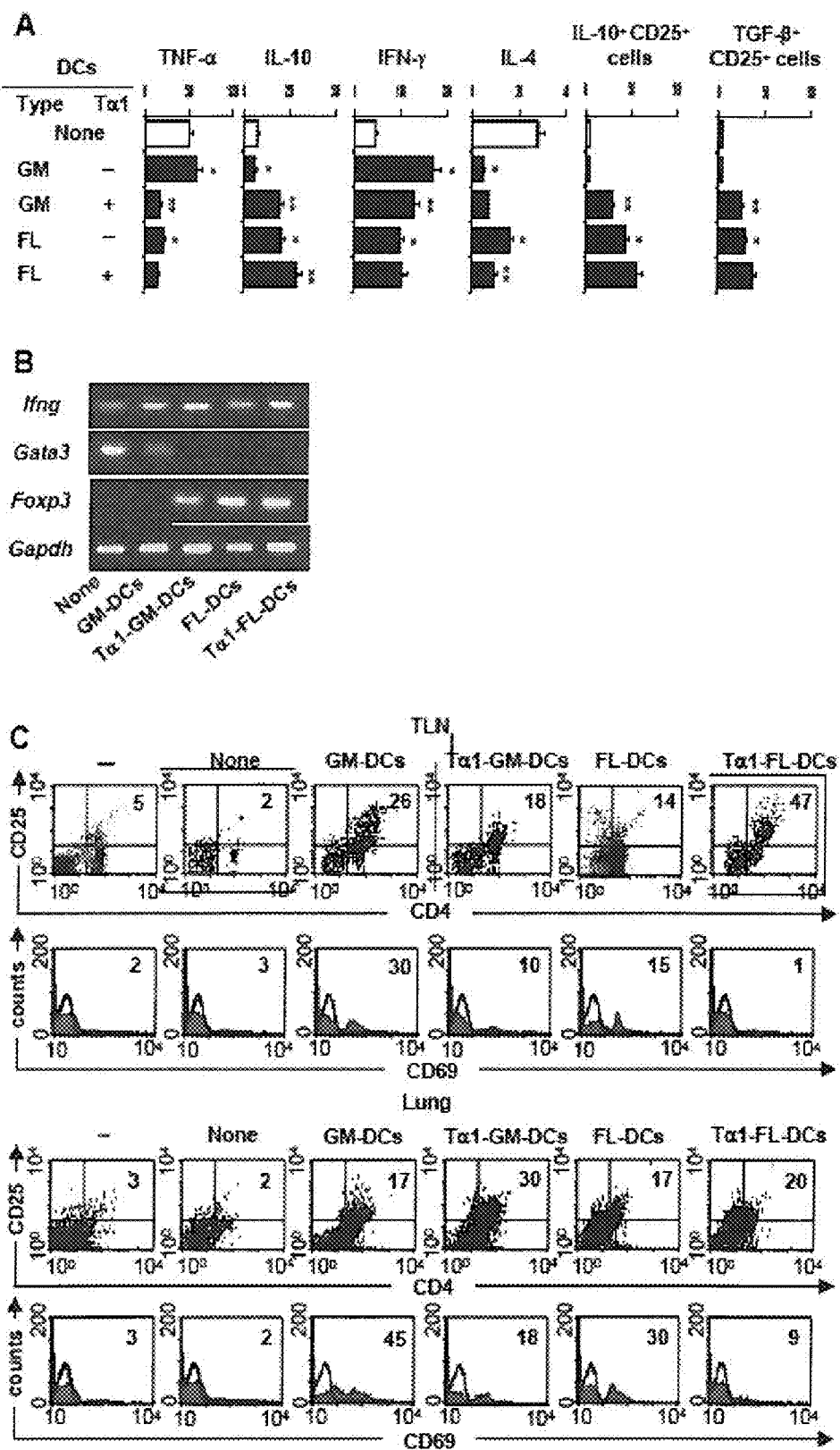

FIG. 4
Thymosin Alpha 1-Induced DCs Prime for Antifungal Th1/T Reg Responses In Vivo Patterns of inflammatory/Th/T reg responses 3 days after the infection in mice treated as in legend to FIG. 2.

(A) TNF-a/IL-10 levels were assessed by specific ELISA in lung homogenates and IFN-γ/IL-4 production were assessed in TLN CD4+ T cells cocultured with Aspergillus-pulsed DCs. Bars indicate standard errors. TLN CD4+CD25+ T cells producing IL-10 or TGF-β were numbered by ELISPOT assay. Results are expressed as the mean number of cytokine-producing cells (±SE) per $2 \times 10^5$ cells. *$P<0.05$, DC-treated versus untreated mice. (**) $P<0.05$, Thymosin alpha 1-treated DCs versus untreated DCs.

(B) Total RNA was extracted from freshly purified CD4+ T cells from TLN of treated or untreated (None) mice. The expressions of the different mRNAs in each cell population were determined by RT-PCR. The expression of a housekeeping gene, Gapdh mRNA, was used as an internal control. The data shown are representative results of three experiments.

(C) Phenotypic analysis of cells isolated from lung or TLN of mice infused or not (None) with different types of DCs, (−) indicating uninfected, untreated mice. CD4+ T cells were sequentially reacted with PE-conjugated anti-CD25 (PC61) and FITC-conjugated anti-CD69 (clone H1.2F3) mAbs. Numbers represent the percentage of positive cells over total cells analyzed. Control staining of cells with irrelevant Ab was used to obtain background fluorescence values. Histograms are representative of one out of four independent experiments.

FIG. 5

Thymosin Alpha 1-Induced T Reg Cells Inhibit Alloreactivity (A) Murine CD4+ T lymphocytes from TLN of transplanted mice were stimulated with irradiated allogeneic splenocytes, autologous splenic DCs stimulated with conidia or Concanavalin A. T cell proliferation was assessed in a 5-day MLR assay and measured by $H^3$ thymidine incorporation over the last 8 hours, (*) P<0.05, transplanted versus donor mice. () P<0.05, T cell- and/or DC-treated mice versus untreated mice. (*) P<0.05, Thymosin alpha 1-treated DCs versus untreated DCs. (B and C) Proliferative activity and IFN-γ production by purified CD4+CD25− T cells from recipient mice against autologous splenic DCs pulsed with *Aspergillus* conidia (B) or allogeneic (BALB/c) splenic DCs (C) in the presence of TLN CD4+CD25+ T cells from recipient mice receiving FL-DCs (a) or Thymosin alpha 1 GM-DCs (b). The data shown are representative results from one of three independent experiments. (*) P<0.05, *Aspergillus*- or alloantigen-specific reactivity versus unstimulated cells.(**) P<0.05, Thymosin alpha 1-treated versus untreated DCs. (D) Peritoneal neutrophils (PMN) were exposed to resting conidia in the presence of lung CD4+CD25+ T cells from FL-DCtreated (a) or Thymosin alpha 1-GM-DC-treated mice (b) for 60 min (for oxidant production, expressed as nanomoles O2-/$10^6$ cells) or 24 hours for cytokine production (pg/mL by ELISA). (*) P<0.05, conidia-exposed versus unexposed PMN. () P<0.05, unexposed versus T reg-exposed PMN. (*) P<0.05, CD25+a) versus CD25+b) T reg.

FIG. 6

Thymosin Alpha 1 Promotes Mobilization and Th1/T reg Antifungal Priming of Human DCs (A) Surface expression of CD11c, CD1a and CD123 on DCs derived from peripheral CD14+ cells of different donors with GM-CSF/IL-4 (GM-DCs) or FLT3L (FL-DCs) in the presence of Thymosin alpha 1. Percent of positive cells is indicated.

(B) Phagocytosis of conidia by GM- or FL-DCs exposed (+) or not (−) to Thymosin alpha 1 from seven recipients of Tcell depleted haploidentical HSCT. The data are the means±SE and expressed as % internalization (numbers within figures). (*) P<0.05, Thymosin alpha 1-treated versus untreated cells.

(C) Cytokine production (pg/mL by ELISA) by Thymosin alpha 1-induced DCs from healthy donors cultured in serum-free medium (1×$10^6$ cells/mL) with unopsonized *Aspergillus* conidia (5×$10^5$/mL) or 10 μg/mL Zymosan or 2 μg/mL CpG-B ODN 2006 for 24 hours. The data shown are aggregated results from three independent experiments and presented in the mean±SD. The detection limits (pg/mL) of the assays were: <3 for IL-12p70, <5 for IL-10, and <3 ng/mL for IFN-a.

(D) Cytokine production by peripheral blood *Aspergillus*-specific CD4+ T cell clones from healthy donors in response to *Aspergillus*-pulsed a1-treated DCs as in A. Bars indicate standard errors. The detection limits (pg/mL) of the assays were: <0.5 for IL-4 and IFN-γ *P<0.05, conidia-stimulated vs unstimulated cells. (**) P<0.05, Thymosin alpha 1exposed versus unexposed cells.

(E) Frequency of *Aspergillus*-specific or alloreactive T cell clones responding to the different types of fungus-pulsed DCs or unpulsed DCs, respectively, from healthy donors or transplanted patients. Growing clones were assessed for specificity after 2 days of stimulation with DCs. (*) p<0.05, GM-DCs versus peripheral blood cells (−). (**) P<0.05, HSCT-DCs versus all other DCs. nd, not done.

The invention claimed is:

1. Method of treating or inhibiting graft-versus-host disease in a mammalian subject, comprising administering an effective amount of thymosin alpha 1 to a mammalian subject suffering from graft-versus-host disease, wherein said effective amount of thymosin alpha 1 is capable of treating or inhibiting said graft-versus-host disease in said mammalian subject and wherein said mammalian subject is the recipient of transplanted cells selected from the group consisting of: stem cells, hematopoietic stem cells and bone marrow.

2. Method according to claim 1, in which the mammalian subject is a human patient.

3. Method according to claim 1, in which the mammalian subject is in myeloablative conditioning regimen.

4. Method according to claim 1, in which the mammalian subject is in a non-myeloablative conditioning regimen.

5. Method according to claim 1, in which the thymosin alpha 1 is administered to the mammalian subject in a pharmaceutically effective amount within a predetermined time window before and/or after the transplantation.

6. Method according to claim 1, in which thymosin alpha 1 is administered to the mammalian subject in combination with an immunosuppressive agent selected from the group consisting of prednisone, methylprednisolone, cyclophosphamide, cyclosporin A, FK506, thalimdomide, azathioprine, Daclizumab, Infliximab, MEDI-205, abx-cbl and ATG.

7. Method according to claim 1, in which the thymosin alpha 1 is administered to the mammalian subject in a dose of from about 10 to 400 μg/kg body weight per day.

8. Method according to claim 7, in which thymosin alpha 1 is administered to the mammalian subject in a dose of from about 40 to 400 μg/kg body weight per day.

9. Method according to claim 8, in which the thymosin alpha 1 is administered to the mammalian subject in a dose of from about 200 to 400 μg/kg body weight per day.

10. Method according to claim 1, in which the thymosin alpha 1 is administered to the mammalian subject in a dose of from about 0.8 to 16 mg per day.

11. Method according to claim 10, in which thymosin alpha 1 is administered to the mammalian subject in a dose of from about 0.8 to 6.4 mg per day.

12. Method according to claim 11, in which the thymosin alpha 1 is administered to the mammalian subject in a dose of from about 1.4 to 2.8 mg per day.

13. Method according to claim 12, in which the thymosin alpha 1 is administered to the mammalian subject in a dose of about 1.6 mg per day.

14. Method according to claim 1, wherein thymosin alpha 1 is administered to the mammalian subject via subcutaneous injection.

* * * * *